(12) United States Patent
Kirsch et al.

(10) Patent No.: US 8,457,765 B2
(45) Date of Patent: Jun. 4, 2013

(54) EAR CLIP WITH POLE

(75) Inventors: Daniel L. Kirsch, Mineral Wells, TX (US); Sai Cheyong Chan, West Kowloon (HK)

(73) Assignee: Electromedical Products International, Inc., Mineral Wells, TX (US)

( * ) Notice: Subject to any disclaimer, the term of this patent is extended or adjusted under 35 U.S.C. 154(b) by 0 days.

(21) Appl. No.: 13/506,143

(22) Filed: Mar. 30, 2012

(65) Prior Publication Data

US 2012/0239127 A1    Sep. 20, 2012

Related U.S. Application Data

(63) Continuation-in-part of application No. 12/591,437, filed on Nov. 19, 2009, now abandoned.

(60) Provisional application No. 61/193,367, filed on Nov. 21, 2008.

(51) Int. Cl.
*A61N 1/04* (2006.01)

(52) U.S. Cl.
USPC .......................................................... 607/149

(58) Field of Classification Search
USPC .......................................................... 607/149
See application file for complete search history.

(56) References Cited

U.S. PATENT DOCUMENTS

| | | |
|---|---|---|
| 4,407,295 A | 10/1983 | Steuer et al. |
| 4,685,464 A | 8/1987 | Goldberger et al. |
| 5,332,401 A | 7/1994 | Davey et al. |
| 5,458,625 A | 10/1995 | Kendall |
| 6,308,104 B1 | 10/2001 | Taylor et al. |
| 2007/0048707 A1 | 3/2007 | Caamano et al. |
| 2007/0219598 A1 | 9/2007 | Rhodes |
| 2008/0249594 A1 | 10/2008 | Dietrich et al. |
| 2008/0288016 A1 | 11/2008 | Amurthur et al. |

FOREIGN PATENT DOCUMENTS

| | | |
|---|---|---|
| DE | 202007016747 | 2/2008 |
| EP | 0323052 | 7/1989 |
| FR | 2513514 | 4/1983 |
| WO | WO2010/059229 | 5/2010 |

*Primary Examiner* — Nicole F Lavert
*Assistant Examiner* — Jeremiah Kimball
(74) *Attorney, Agent, or Firm* — Welsh Flaxman & Gitler LLC

(57) ABSTRACT

An ear clip electrode used to conduct a minute amount of electricity from a stimulator to the ear lobes of a patient. The ear clip electrode is provided with an inner and outer plastic piece onto which separate metallic plates are placed. Both the metallic plate as well as the plastic pieces are provided with a circular end onto which a metallic pole is placed. Electrode pads are placed upon these metallic poles and electricity is conducted from each of the plates to the electrode pad and then to the patient's ear lobe. A plastic shroud is placed over a substantial length of each of the metallic plates. Plastic material also covers the end surface of each of the metallic poles. The ear clip electrode is connected to a source of minute electrical energy.

9 Claims, 6 Drawing Sheets

EAR CLIP WITH POLE

CROSS REFERENCE TO APPLICATION(S)

This application is a continuation-in-part of U.S. patent application Ser. No. 12/591,437, filed Nov. 19, 2009, entitled "EAR CLIP WITH POLE", which is abandoned. This application claims the benefit of U.S. Provisional Patent Application Ser. No. 61/193,367, filed on Nov. 21, 2008, entitled "EAR CLIP WITH POLE", which is expired.

FIELD OF THE INVENTION

The invention is directed to an ear clip used to transmit a relatively small value of electrical current to the ear lobes of a patient.

BACKGROUND OF THE INVENTION

The application of electro-medical currents is not a new concept. Ancients recognized the therapeutic value of naturally occurring electrical phenomena long before William Gilbert defined electricity in 1600. Both Aristotle and Plato referred to the Black Torpedo (electric ray fish) prescribed in 46 AD by the physician Scribonius Largus for the relief of a variety of medical conditions from headaches to gout (head to foot). In the 1800s dentists reported pain reduction using early and somewhat crude electro-medical devices.

By the late 1800s electrical devices were in widespread use to manage pain and claimed to cure a variety of medical disorders. The exuberant claims of unrefined early electrical technologies facilitated by the political clout of the pharmaceutical lobbies caused this form of therapy to fall into disrepute by the medical profession in the early part of the 20th century. As a result, medical colleges stopped teaching electrotherapeutics. Biophysics was virtually eliminated from medical practice leaving chemistry as the master science and with it the burden of responsibility for curing all disease. Now, in the 21st century it is clear that chemistry as the sole therapeutic model for medicine has not lived up to its promise causing modern medicine to reexamine the potential of biophysics.

Experimentation with low intensity electrical stimulation of the brain was first reported by Drs. Leduc and Rouxeau of France in 1902. Initially, this method was called electro-sleep as it was thought to be able to induce sleep. Research on using what is now referred to as Cranial Electrotherapy Stimulation (CES) for treatment of anxiety, insomnia and depression began in the Soviet Union during the 1950s and first came to the United States in the 1960s.

In 1965 Drs. Ronald Melzack of Canada and Patrick Wall of the United Kingdom published a paper explaining a new comprehensive theory of how pain is processed by the nervous system. Their Gate Control theory also explained how electrical stimulation can influence the physiology of pain pathways. By 1967 electrical devices were surgically implanted to control severe low back pain. Surface electrical stimulation devices were used to test the person's response as a means of screening surgical candidates and to determine the most effective electrode site for implantation. It was soon discovered that electro-medical treatment through the skin (transcutaneous) was equally effective and could be used for pain relief alone, avoiding surgery. Since then, these devices, known as transcutaneous electrical nerve stimulators (TENS) have become widely accepted by health care practitioners to control many forms of pain. TENS technology is based on the concept of using electricity as an overriding force. Repeatedly tapping a painful area with a blunt object, such as a pen or a spoon might produce a similar effect. That is why TENS is referred to as counter-irritation analgesia. There is virtually no residual effect with TENS and the people who use it develop a tolerance to electrical therapy.

All life is of an electrochemical nature. There are extensive electrical fields at work throughout the universe and the body. The nervous system, for example, has long been known to work through both electrochemical and purely electrical signals. In fact, all molecules are held together by electrical bonding at the atomic level. Basic science research into the nature of bioelectrical control systems in humans and animals led medical scientists such as Dr. Robert O. Becker of the United States and Dr. Björn Nordenström of Sweden (who served as Chairman of the Nobel Assembly) to propose completely new theories of physiology based on our latest understanding of biophysics.

Alpha-Stim® technology incorporates these theories and is proven more efficacious than most other treatments for the conditions it treats. It is a viable alternative to traditional TENS, as well as an alternative or complementary treatment with pharmacological management, surgery and other interventions. The original Alpha-Stim® Model 2000 weighed 40 pounds and cost $5,850 when it was first introduced in 1981. The Alpha-Stim® M microcurrent stimulator utilizes the most advanced technology available today. It is now possible, in most cases, to alleviate anxiety, insomnia, depression and pain with far less current than used in previous technologies, and experience long term and cumulative relief with as little as only a few minutes of treatment time.

U.S. patent application Ser. No. 12/588,647, filed on Oct. 22, 2009, which has been published as U.S. patent application publication No. 2010/0145410, described the use of a cranial electrotherapy stimulator (CES) used to treat anxiety, insomnia and depression in which ear clip electrodes are attached to both of the ear lobes of the patient. Very small electrical currents as described in the aforementioned U.S. patent application are transmitted to the ear lobes of the patient through ear clip electrode pads to treat anxiety, insomnia and depression. Since minute electrical currents are transmitted from the CES to the ear lobes of the patient and thereafter into the patient's brain, it is important that the ear clip electrode pads maintain firm contact with the patient's ear lobes. Prior art ear clip electrode pads would become easily dislodged from the patient's ear lobes from a slight movement of the patient's head and body. This is caused by the fact that the prior art ear clip electrodes were held in place solely by a double-sided adhesive tape. Since the adhesiveness of the tape degrades with moisture on the surface of electrode pads, the prior art electrode pads would tend to slip from the ear lobes of the patient and thereby not provide the appropriate contact.

SUMMARY OF THE INVENTION

The disadvantages and deficiencies of the prior art ear clip are addressed by the present invention. Each ear clip of the present invention would include a pair of longitudinally shaped inner and outer pieces biased towards one another utilizing a spring. These pieces are generally constructed from a plastic material, for insulation purposes and ease of handling. Each of the plastic pieces contains a metallic plate in which electricity is transmitted to respective ear clip electrode pads generally constructed from a felt material used to conduct the minute electricity from the CES to the patient's ear lobes. Additionally, each of the metallic plates includes a circular end portion. A wire is provided between the CES device and one of the metallic plates allowing the minute amount of electricity to be introduced to the patient's brain. Metallic poles are mechanically fixed to circular end portions of each of the plates to hold the ear clip electrode pads in place. The metallic poles can be fabricated from stainless steel or similar metals. These poles are used in conjunction with a double-sided adhesive tape to securely affix the ear clip electrode pads to the patient's ear lobes. The electrode pads are provided with a central hole through which the metallic poles pass. This configuration makes it impossible for electrode pads to be displaced from the metallic poles. Although one ear clip is shown herein, it is appreciated that one ear clip would be in contact with one of the patient's ear lobes, and a second ear clip would be in contact with the patient's second ear lobe.

A shroud covers each of the metallic plates between the spring and the circular end portions. The shrouds are constructed from a plastic material, similar to the plastic material of the longitudinally shaped inner and outer pieces. Each of the plastic pieces is provided with a pair of arms extending between the spring and the circular end portions. Each of the shrouds is secured between the arms of each of the plastic pieces to prevent inadvertent contact of the metallic plate by dirty or greasy fingers.

BRIEF DESCRIPTION OF THE DRAWINGS

For a better understanding of the invention and to show how the invention may be carried to effect, reference will now be made, purely by way of example, to the accompanying drawings with like elements utilizing the same reference numbers in which.

DETAILED DESCRIPTION OF THE PRESENT INVENTION

Figure 1:
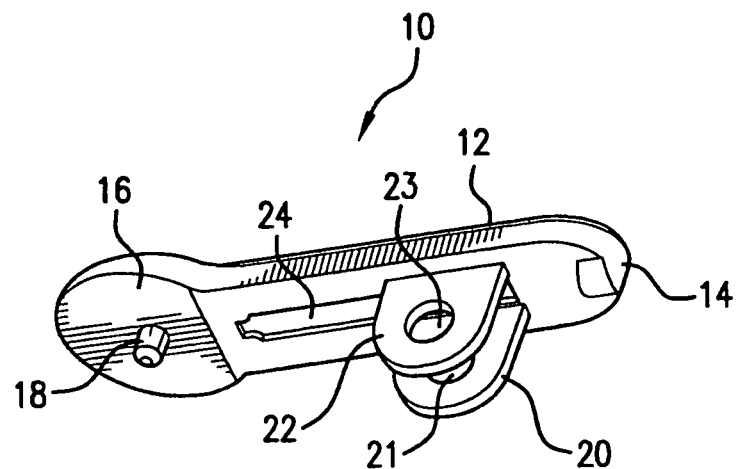
FIG. 1 is a perspective view of one of the plastic pieces.
Figure 2:
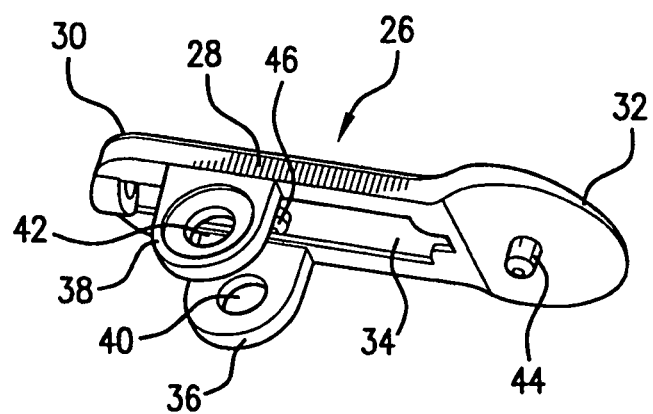
FIG. 2 is a perspective view of the second plastic piece.
Figure 5:
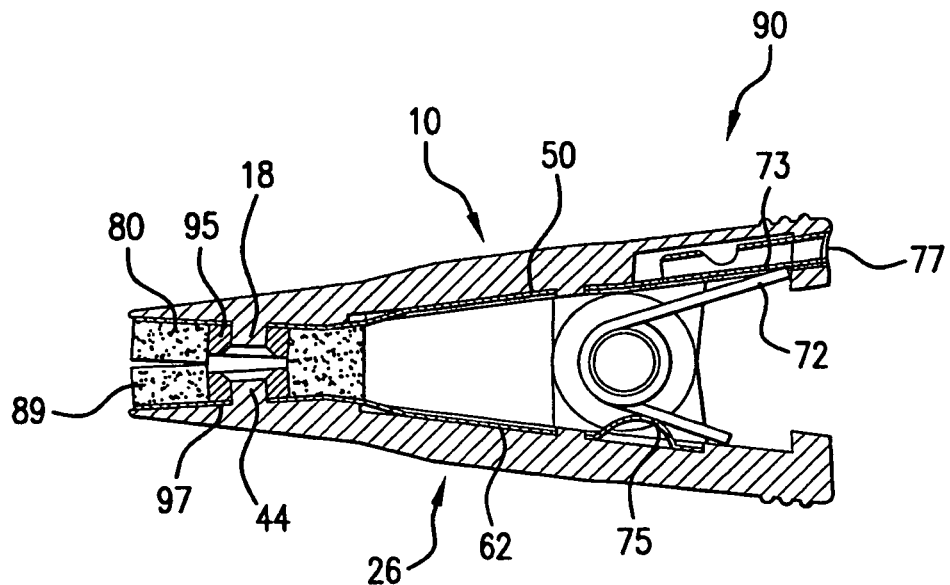
FIG. 5 is a side view of the completed ear clip when it is biased in the closed position.
Figure 6:
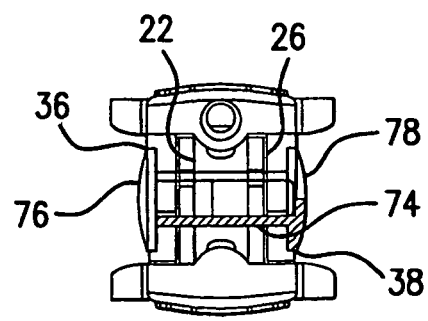
FIG. 6 is an end view of the ear clip electrode shown in FIG. 5.

FIGS. 1 and 2 illustrate one piece 10 (FIG. 1) and a second piece 26 (FIG. 2) which are connected together to form a complete ear clip 90 as shown in FIGS. 5 and 6. For ease of explanation, the piece 10 which will be referred to as an outer piece generally constructed from a plastic material including a longitudinal section 12 provided between an end section 14 corresponding to a handle section and a circular section 16 onto which an electrode pad would be attached. As will be subsequently explained, the end of the longitudinal section 12 close to the end section 14 would include two holding devices 20, 22. A hole 21 is provided in the holding device 20 and hole 23 is provided in the holding device 22. A small plastic rod 18 is attached to the circular section 16 of the outer piece 10, the purpose of which will be explained. The longitudinal section 12 would include a longitudinal cutout 24 extending for almost the entire length of the longitudinal section 12.

As shown in FIG. 2, a piece 26 which will be referred to as an inner piece is constructed of a plastic material similar to the plastic outer piece 10 shown in FIG. 1. This plastic inner piece 26 would include a longitudinal section 28 provided between an end section 30 corresponding to a handle section and a circular section 32 onto which an electrode pad will be attached which is also similar to the circular section 16 of the outer piece 10. A rod 44, which can be constructed from a plastic material, is attached to the circular portion 32 of the inner piece 26. When constructed as shown in FIG. 5, each of the rods 18, 44 would be directed toward one another. The longitudinal section 28 would include a cutout 34 extending for almost the entire length of the longitudinal section 28. Extending from the end of the longitudinal section 28 close to the end section 30 would be two additional holding devices 36, 38. Holding device 36 would be provided with a hole 40 within the center therein and holding device 38 will be provided with a hole 42.

When the plastic outer piece 10 and the plastic inner piece 26 are connected together as shown in FIGS. 5 and 6, the holding pieces 36 and 38 of the plastic inner piece 26 would be on the outside of the ear clip and the holding pieces 20 and 22 of the plastic outer piece 10 as shown in FIG. 1 would be inside of the holding pieces 36 and 38. A plastic pin 74, with an integrated end cap 78, would extend through the holes 21, 23, 40, 42 and holding pieces 20, 22, 36 and 38 would be secured by end cap 76 to secure the outer piece 10 and the inner piece 26 together.

Figure 3:
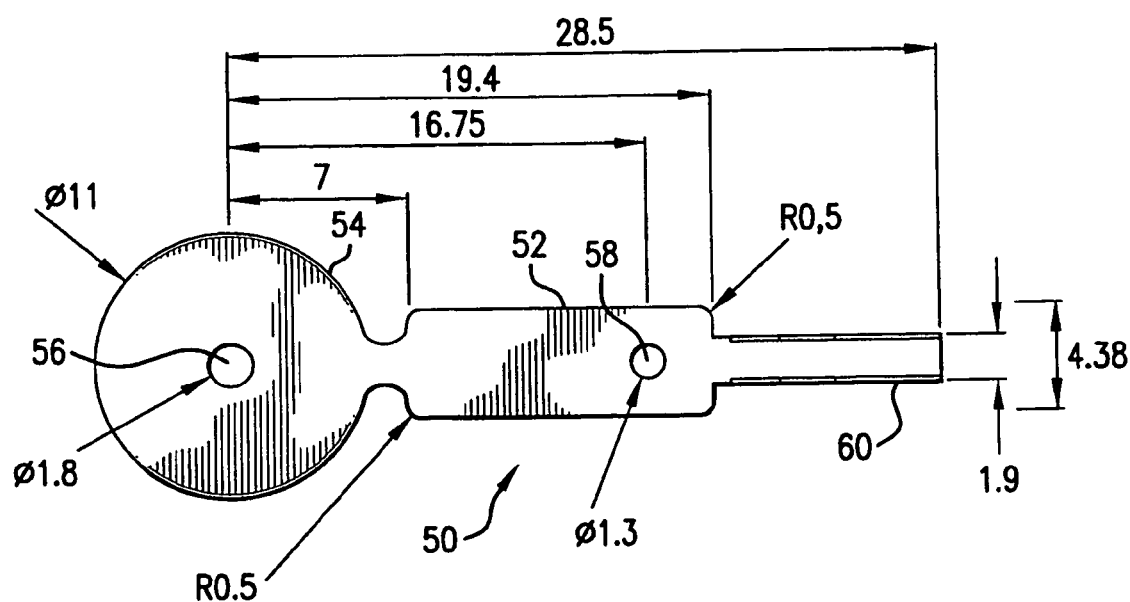
FIG. 3 is a top view of one of the metallic plates.

A complete ear clip would include a metallic plate 50 such as constructed from stainless steel as shown in FIG. 3. This plate would have a longitudinal section 52 having a hole 58 therein and a circular distal end section 54 having hole 56 therein. A thinner longitudinal section proximal 60 would be connected to the longitudinal section 52. This longitudinal section 60 would be connected to a wire 81 which is in turn connected to the CES device. The wire 81 would extend through a hole 83 in the end portion of the outer plastic piece 10. This metallic plate 50 would be inserted into the cutout portion 24 of the outer piece 10. The hole 56 of the circular portion 54 would be inserted over the rod 18. The hole 58 of the metallic plate 50 is mounted on a rod (not shown) of the plastic outer piece 10. The rod is then collapsed by heat to join the metallic plate 50 to the plastic outer piece 10.

Figure 4:
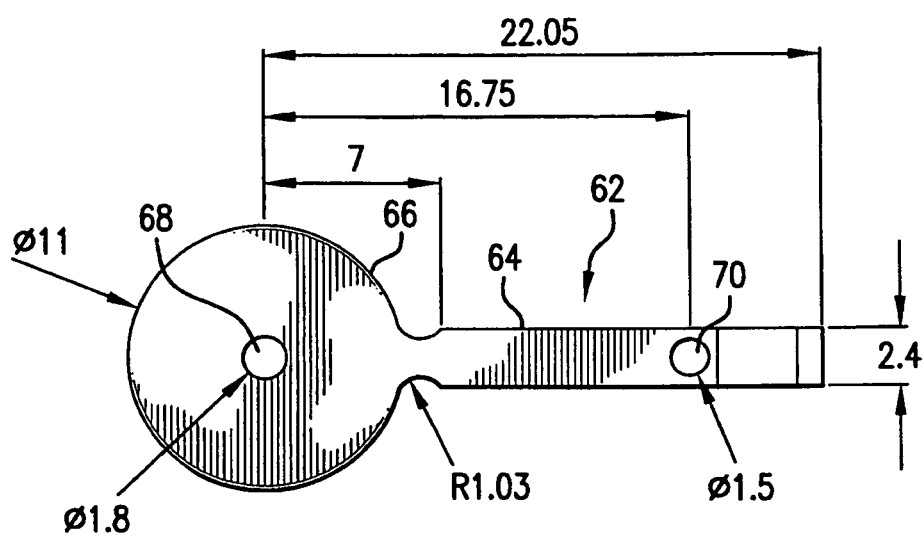
FIG. 4 is a top view of the second of the metallic plates.

As shown in FIG. 4, a metallic plate 62 which can be constructed from stainless steel contains a longitudinal portion 64 connected to a circular portion distal 66 having a hole 68 therein. A hole 70 is provided in the proximal end longitudinal portion 64. This plate 62 is shorter in length than the plate 50. The plate 62 would be inserted into the cutout 34 of the inner plastic piece 26, with the rod 44 inserted into the hole 68. Similar to the metallic plate 50, the metallic plate 62 is mounted on a rod (not shown) of the plastic inner piece 26. The rod is then collapsed by heat to join the metallic plate 62 to the plastic inner piece 26.

Figure 7:
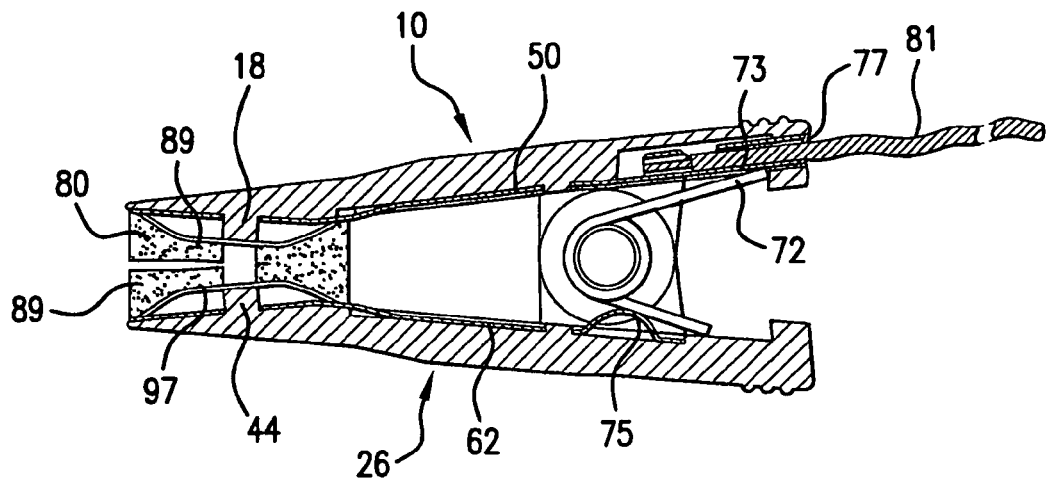
FIG. 7 is a side view of a prior art ear clip.

A prior art ear clip 93 is shown in FIG. 7. This prior art ear clip does include a metallic plate 50 connected to the outer plastic piece 10 as well as a metallic plate 62 connected to the inner plastic piece 26. However, the circular portion of the metallic plate 50 has a convex portion 89 and the circular portion of the metallic plate 62 has a convex portion 91. This was done to reduce the distance and hence the electrical resistance between these surfaces and the patient's ear lobe. It is important to note that the present invention does not contain these convex portions and the circular portions 54, 66 lie flat. This is due to the fact that, as shown in FIG. 5, a stainless steel pole 95 is attached to the circular end 54 of the metallic plate 50 and a stainless steel pole 97 is attached to the circular portion 66 of the metallic plate 62. The pole 95 would be provided around the rod 18 and the pole 97 would be provided around the rod 44.

Prior art plates similar to the plates 50 and 62 were made slightly convex to reduce the distance and hence the electrical resistance between these surfaces and the patient's earlobe. The present invention is not convex and the circular portions 54, 62 lie flat. This is due to the fact that the poles 95 and 97 stick out from the circular services and have therefore already reduced the distance between these surfaces and the ear lobe.

As shown in FIG. 5, a spring 72 which can be constructed from stainless steel or any other appropriate material would be wound around the plastic pin 74 which biases the ear clip electrode in the close position as shown in FIG. 5 when it is attached to the patient's ear lobe. The spring 72 is also used to connect the plate 50 to the plate 62 as shown in FIG. 5. The end of the spring 72 contacts the metallic plate 50 at point 73. Additionally, a portion of the spring 72 will contact a convex portion 75 of the metallic plate 62. This is important since a wire extending from the CES to the ear clip electrode would contact the plate 50 at point 77, and would allow electricity to contact the plate 62 at portion 75.

Figure 8:
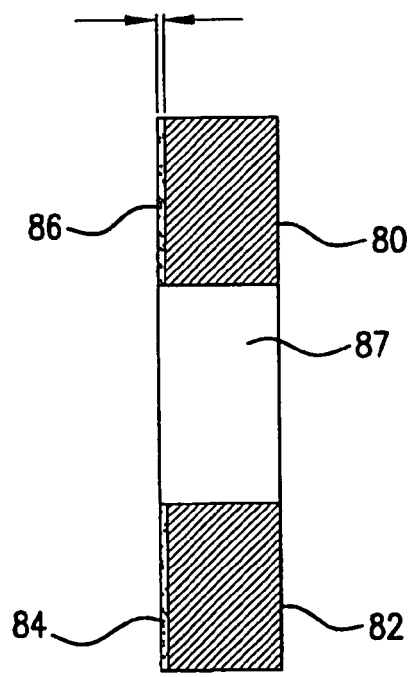
FIG. 8 is a side view of one of the electrode pads.

FIG. 8 shows ear clip electrode pad 80, 82 which would be attached to one of the metallic poles 95, 97. A hole 87 would allow the electrode pad 80 to be provided over one of the metallic poles 95, 97. Each electrode pad 80, 82 would be provided on one of the metallic poles 95, 97. Each of the electrode pads would then be attached to one of the circle ends of the metallic plates 50 or 62. Each of the electrode pads is a small piece of a donut-shaped cotton pad having a double-sided adhesive tape 84, 86 at its bottom. It is wetted with saline to enable it to conduct electricity. When each of the electrode pads wears out, they can be easily replaced. Each of the poles will be used to prevent the electrode pads from slipping sideways.

When the clip electrode shown in FIG. 5 is in use, a miniature electrolysis process is produced, resulting in the metallic plates 50, 62 attracting dirt and grease in the vicinity of the metallic plates 50, 62. Impurities in the conducting solution would also be deposited onto the metallic plates 50, 62. The stain that accumulates on the metallic plates 50, 62, over time, would look like rust, thereby resulting in an unpleasant appearance, as well as affecting the operability of the clip electrode.

Figure 9:
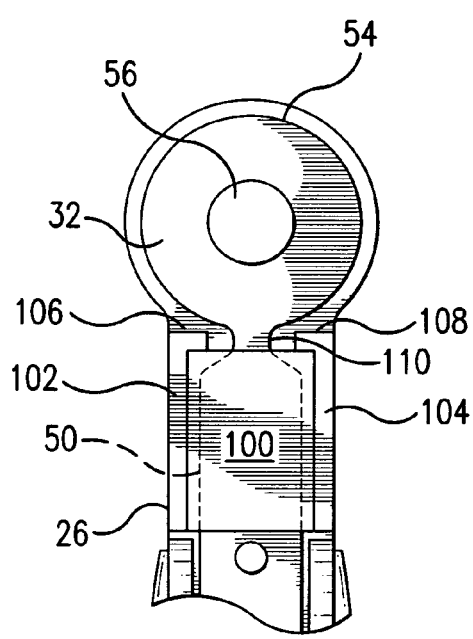
FIG. 9 is a top view of the shroud applied over one of the metallic plates.
Figure 10:
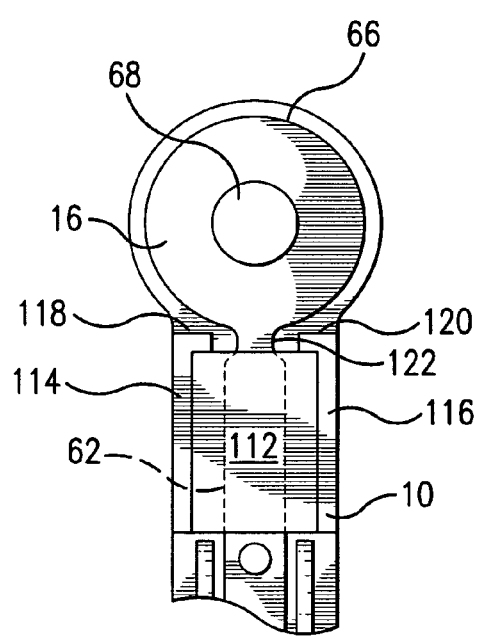
FIG. 10 is a top view of the shroud applied over the second of the metallic plates.

Therefore, and in accordance with an alternate embodiment, FIGS. 9 and 10 disclose an ear clip wherein a substantial portion of the metallic plates 50, 62 is shrouded with a plastic material. As shown in FIG. 9, a first plastic shroud 100 is secured over a substantial length of the metallic plate 50. Large plastic legs 102, 104 are fixedly attached to the edges of the plastic inner piece 26 (as shown in FIG. 2) from close to the ends of the holding devices 36, 38 (shown in FIG. 2) and extend to the circular portion 32. The plastic shroud 100 is generally rectangular in shape and includes a top, relatively flat surface, facing away from the metallic plate 50, and a bottom, relatively flat surface facing the metallic plate 50. A small arm piece 106 is fixedly attached to the side edges of the plastic inner piece 26 and extends transversely with respect to one end of large leg 102. A small arm piece 108 is fixedly attached to one end edge of the plastic inner piece 26 and extends transversely with respect to one end of large leg 104 in the direction of the small arm 106. The plastic shroud 100 is secured between the large arms 102, 104 and the small arms 106, 108, covering substantially the entire length of the metallic plate 40, with the exception of portion 110.

FIG. 10 illustrates the use of a second plastic shroud 112 secured over a substantial length of the metallic plate 62. The plastic shroud 112 is generally rectangular in shape and includes a relatively flat top surface facing away from the metallic plate 62, and a bottom, relatively flat surface, facing the metallic plate 62. Large plastic legs 114, 116 are fixedly attached to the edges of the plastic outer piece 10 from close to the ends the holding devices 20, 22 (see FIG. 1) and extends to the circular portion 16. A small arm piece 118 is fixedly attached to one end edge of the outer piece 10 would extend transversely with respect to one end of the large plastic leg 114. A small arm piece 120 is fixedly attached to the same end edge as the arm piece 118 of the outer piece 10 and extends transversely with respect to one end of the large leg 116 in the direction of the small leg 118. The plastic shroud 112 is secured between the large arms 114, 116 and the small arms 118, 120 covering substantially the entire length of the metallic plate 62, with the exception of portion 122.

Additionally, and with reference to the embodiment disclosed in FIG. 5, it is noted that the ends of the metallic poles 95, 97 are also coated with a plastic material covering the entire end surface of the metallic poles 95, 97. The plastic shrouds 100, 112 along with the plastic covering the ends of the metallic poles 95, 97 would prevent inadvertent handling of the metallic plates 50, 62, as well as the metallic poles 95, 97, thereby preventing the deposition of impurities on these surfaces, such as impurities from an individual's hands and fingers, as well as the utilization of a conductive solution. The shrouds 100, 112 would, therefore, cover any unsightly stains as well as ensuring that the electrode clip operates efficiently. The embodiment shown in FIGS. 9 and 10 in which plastic shrouds 100 and 112 cover the metallic plates 50 and 62 respectively, would also include the plastic material covering the entire end surfaces of the metallic plates 95, 97.

The present invention may be embodied in other specific forms without departing from the spirit or central characteristics thereof. The present embodiments are therefore to be considered in all aspects as illustrative but not restrictive, and the scope of the invention being indicated by the appended claims rather than by the foregoing description, and all changes which come within the immediate range of equivalence of the claims are therefore intended to be embraced therein.

What is claimed is:

1. A clip adapted for attachment to an individual's ear lobe, comprising:
 a longitudinally shaped outer piece including a first handle section and a first electrode contact section;
 a longitudinally shaped inner piece including a second handle section and a second electrode contact section;
 a pin connecting said outer piece to said inner piece;
 a first metallic pole provided in said first electrode contact section;
 a second metallic pole provided in said second electrode contact section;
 a first non-metallic electrode in contact with said first metallic pole; and
 a second non-metallic electrode in contact with said second metallic pole;
 a first metallic plate having a distal end and a proximal end provided in said outer piece extending from said first handle section to said first electrode section, said distal portion of said first metallic plate being flat;
 a first shroud provided over said first metallic plate concealing said first metallic plate from view;
 a second metallic plate provided in said inner piece extending from said second handle section to said second electrode contact section, said second metallic plate having a flat distal end and a proximal end; and a second shroud provided over said second metallic plate concealing said second metallic plate from view;

wherein the clip is adapted for application to the ear lobes of the individual, allowing said first and second electrodes to contact the ear lobe of the individual.

2. The clip in accordance with claim 1, further including a metallic spring coiled around said pin for biasing the clip in the closed position, said first metallic plate in contact with said metallic spring and said first metallic pole and said second metallic plate in contact with said metallic spring and said second metallic pole.

3. The clip in accordance with claim 2, wherein the proximal end of said first handle section is provided with a hole allowing a wire attached to an electrical power source to contact the proximal end of said first metallic plate.

4. The clip in accordance with claim 2, further including a first rod attached to said first electrode contact section, such that said first rod would extend through a hole provided in the distal end of said first metallic plate and further including a second rod attached to said second electrode contact section, such that said second rod would extend through a hole provided in the distal end of said second metallic plate.

5. The clip in accordance with claim 1, wherein said first metallic pole surrounds said first rod and said second metallic pole surrounds said second rod.

6. The clip in accordance with claim 1, wherein said first and second shrouds are constructed from a plastic material.

7. The clip in accordance with claim 1, wherein said longitudinally shaped outer piece is provided with a first set of arms for securing said first shroud to said longitudinally shaped outer pieces, and said longitudinally shaped inner piece is provided with a second set of arms for securing said second shroud to said longitudinally shaped inner piece.

8. The clip in accordance with claim 7, wherein said first set of arms comprises two first long arms, each first long arm extending along one side of said longitudinally shaped outer piece, and two first short arms, each of said two first short arms extending transversely from one end of one of said first long arms, and further wherein said second set of arms comprises two second long arms, each second log arm extending along one side of said longitudinal shaped inner piece, and two short second arms, each of said two short arms extending transversely from one end of one of said second long arms.

9. The clip in accordance with claim 1, wherein each of said first and second metallic poles include an end surface covered by a plastic material.

\* \* \* \* \*

UNITED STATES PATENT AND TRADEMARK OFFICE
CERTIFICATE OF CORRECTION

PATENT NO. : 8,457,765 B2  
APPLICATION NO. : 13/506143  
DATED : June 4, 2013  
INVENTOR(S) : Daniel L. Kirsch et al.

Page 1 of 1

It is certified that error appears in the above-identified patent and that said Letters Patent is hereby corrected as shown below:

Title Page, Item (75) Inventors, the second inventor's name should read --Sai Cheong Chan--.

Signed and Sealed this  
Sixteenth Day of July, 2013

Teresa Stanek Rea  
*Acting Director of the United States Patent and Trademark Office*